United States Patent [19]
Powers

[11] Patent Number: 5,967,784
[45] Date of Patent: Oct. 19, 1999

[54] HAND HELD DEVICE FOR REDUCING THE DISCOMFORT ASSOCIATED WITH THE ADJUSTING OF ORTHODONTIC APPLIANCES

[76] Inventor: Michael J. Powers, 4711 Gabriel Way, La Mesa, Calif. 91941

[21] Appl. No.: 09/114,697

[22] Filed: Jan. 13, 1998

[51] Int. Cl.$^6$ .................................................. A61C 5/00
[52] U.S. Cl. ............................... 433/229; 433/2; 601/38; 601/72; 601/142
[58] Field of Search ............................. 433/2, 5, 6, 229; 601/38, 67, 70, 72, 139, 142

[56] References Cited

U.S. PATENT DOCUMENTS

| | | |
|---|---|---|
| 1,826,434 | 10/1931 | Reiss . |
| 1,953,088 | 4/1934 | Purdy . |
| 3,098,298 | 7/1963 | Cerveris . |
| 3,115,139 | 12/1963 | Schneider . |
| 4,011,616 | 3/1977 | Kennedy . |
| 4,123,844 | 11/1978 | Kurz . |
| 4,162,576 | 7/1979 | Takemoto et al. . |
| 4,348,178 | 9/1982 | Kurz .............................................. 433/6 |
| 5,030,098 | 7/1991 | Branford .................................. 433/229 |
| 5,374,237 | 12/1994 | McCarty, Jr. .............................. 601/38 |
| 5,467,785 | 11/1995 | McCarty, Jr. .............................. 601/38 |
| 5,551,952 | 9/1996 | Falgout ..................................... 601/139 |
| 5,683,421 | 11/1997 | Guarini, Jr. et al. .................... 601/142 |
| 5,711,759 | 1/1998 | Smith et al. ............................. 601/139 |

*Primary Examiner*—Ralph A. Lewis
*Attorney, Agent, or Firm*—Frank D. Gilliam

[57] ABSTRACT

A dental patient hand held vibrating device having a interdental mouthpiece portion for insertion into the mouth for gripping between the teeth of the dental patient encountering discomfort resulting from the adjustment of their orthodontic appliances. The hand held device comprises a housing containing a battery and a switch for selectively operating a motor with an off center weight attached to the motor rotating shaft for creating a high frequency vibration that vibrates the entire device. The vibration is transferred from the body of the device to the interdental mouthpiece held between the teeth of the patient. The vibrating interdental mouthpiece reestablishes an adequate blood supply to the teeth and surrounding periodontal structures so as to substantially eliminate the discomfort encountered by a patient that has had their orthodontic appliance adjusted.

9 Claims, 2 Drawing Sheets

HAND HELD DEVICE FOR REDUCING THE DISCOMFORT ASSOCIATED WITH THE ADJUSTING OF ORTHODONTIC APPLIANCES

BACKGROUND OF THE INVENTION

The invention relates to hand held apparatus for utilizing a vibrating interdental mouthpiece to eliminate the discomfort caused by the adjustment of the dental patient's orthodontic appliances.

There are several patents directed to various elaborate professional apparatus utilized by Dentists in their offices for multiple purpose one of which is reducing discomfort for the orthodontic patient.

U.S. Pat. Nos. 4,123,844; 4,229,165; 4,244,688; 4,348,177; 4,348,178 and 4,382,780 all by inventor Craven H. Kurz teach various apparatus and methods for the purpose of decreasing overall treatment time and reducing bone and root loss in a pain free environment. These devices appear to be complex professional dental equipment for use under the supervision of a dental professional in a dental office atmosphere.

There has not been a inexpensive portable unit that can be used by the patient in a non-dental office environment which has a disposable interdental mouthpiece that can easily be replaced if it becomes damaged or contaminated.

SUMMARY OF THE INVENTION

The device of the invention comprises in one embodiment a hand held plastic housing containing a battery operated motor which operates at high revolutions, a weight being attached to the motor shaft in an off center position which when the motor is operated cause the entire housing and contents therein to vibrate at a very fast rate, a battery and a switch for selectively connecting the battery to the motor for operation thereof. A interdental mouthpiece in the general shape of a dental arch is attached to the end of the housing remote from the battery and switch. The interdental mouthpiece is attached in a position normal to the housing length by means of a loop at the end opposite to the end to be held in the mouth of the patient. The loop's interior diameter is the same diameter as that of the attached body of the housing which provides a snug selectively removable friction attachment to the housing. The interdental mouthpiece can be easily removed and a second interdental mouthpiece can be readily attached on the same apparatus body. When replacement is required because of damage or contamination any number of interdental mouthpieces can be utilized separately on the same housing.

In a second embodiment, the housing is positioned parallel to the interdental mouthpiece, the interdental mouthpiece is inserted within a slot in the side of a connector positioned between and connecting an adjacent pair of housings. And is locked thereon by means of a protrusion in the housing and a concave dimple in the interdental mouthpiece for mating with the protrusion. The interdental mouthpieces is constructed to have a tight or snug fit into the slot. Different interdental mouthpieces can be forced into the slot and forced out, but will not accidentally become detached from the housing during operation of the device. This second embodiment has a bifurcated housing with the motor and concentric weight in one bifurcation and the battery in the second bifurcated portion with the connector therebetween containing the slot for the interdental mouthpiece.

The interdental mouthpiece is formed in the general shape of a dental arch has a thickness of from two to five millimeters and a maximum width in the range of ten to fifteen millimeters.

The interdental mouthpiece is constructed of soft flexible material such as plastic, rubber, dental acrylics, silicon based products or the like having the properties of being firm, dense enough to transmit the vibrations from the housing and flexible enough to adapt to the misaligned teeth found in orthodontic patients.

The housing generally consists of two or more removable sections constructed from any convenient material and such as plastic, metal or the like suitable for the purpose intended. The power supply battery can be rechargeable or the throwaway type commonly available.

The principle object of this invention is to provide a patient fitted with orthodontic appliances a personal apparatus to reduce the discomfort caused by the adjustments of the appliance.

Another object of this invention is to provide the patient with a hand held vibrating device equipped with a interdental mouthpiece that vibrates the teeth of the patient when gripped between that patient's teeth to ease or eliminate discomfort caused by the adjustment of the orthodontic appliance worn by that patient.

Another object of this invention is to provide a vibrating device for easing the discomfort associated with the adjustment of orthodontic appliances that can be used by the dental patient independent of professional dental assistance.

Yet another object of this invention is to provide each dental patient wearing orthodontic appliances a simple and inexpensive device for eliminating discomfort from the appliances.

These and other objects, features and advantages of the present invention will become apparent from the following description when take with the accompanying drawing Figures.

BRIEF DESCRIPTION OF THE DRAWING FIGURES

DETAILED DESCRIPTION OF THE PREFERRED EMBODIMENTS OF THE INVENTION

Figure 1:
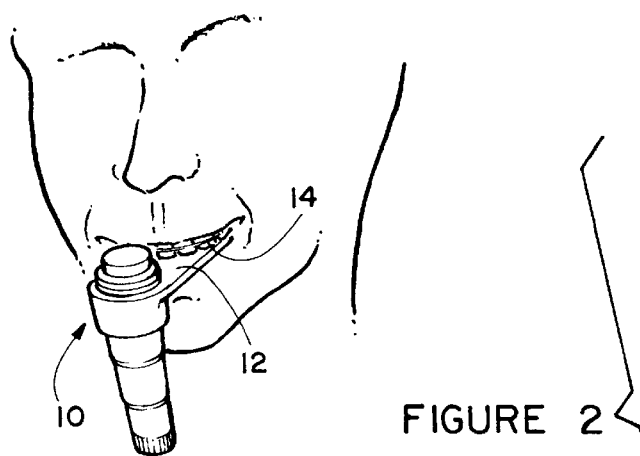
FIG. 1 depicts one embodiment of the device of the invention positioned for use in the mouth of a patient wearing an orthodontic apparatus.
Figure 2:
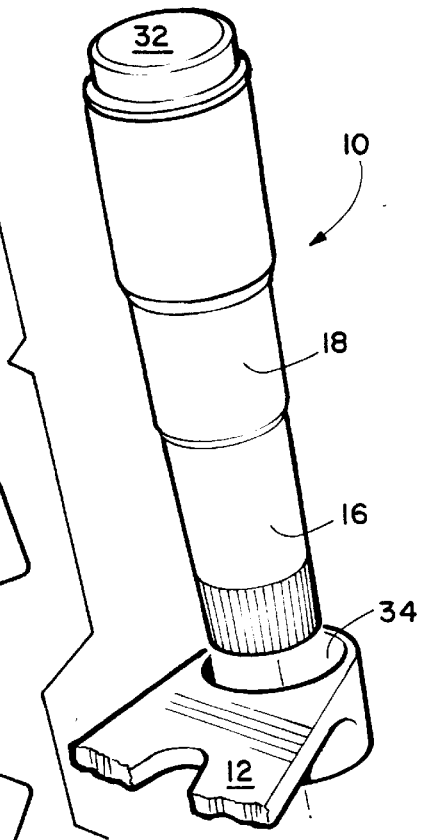
FIG. 2 is a perspective showing of the first embodiment with the interdental mouthpiece separated from the vibration body portion.
Figure 3:
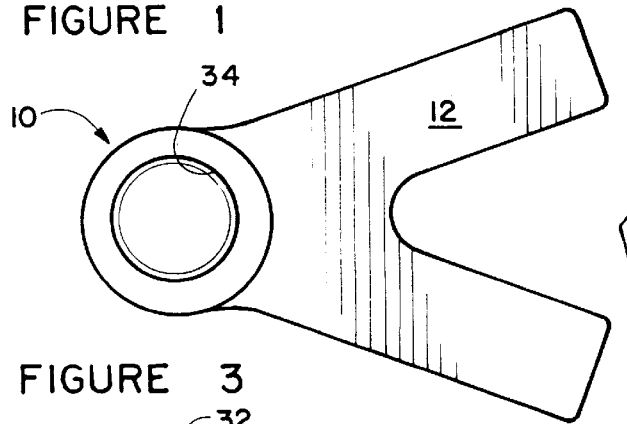
FIG. 3 depicts a top view of the device of FIG. 2.
Figure 4:
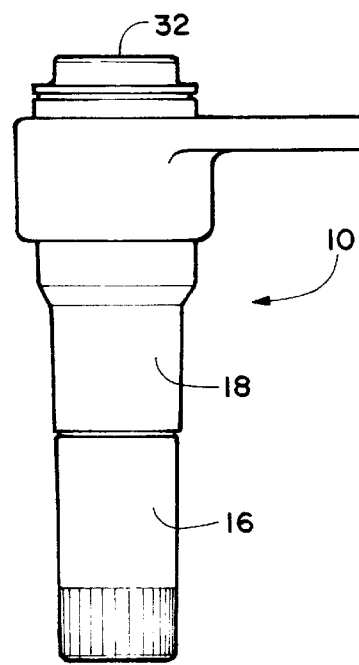
FIG. 4 is a side view of the device of FIG. 2.
Figure 5:
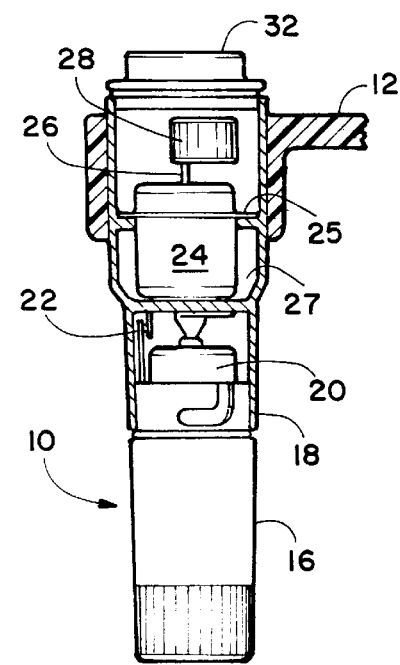
FIG. 5 is a partial cutaway showing of the device of FIG. 2.

Referring now to FIGS. 1–5. FIG. 1 is a showing of the vibrating device 10 of the invention positioned for use with the interdental mouthpiece 12 inserted into the mouth of the patient wearing an orthodontic appliance 14 for straightening of the patient's teeth or the like.

Referring now to drawing FIGS. 2–5, the device 10 comprises a two part body portion 16 and 18. Body portion 16 houses a battery power supply 20 and a power connecting means 22.

The upper body portion 18 houses a motor 24 held in position by a intermediate plate 25 which grips the side walls of the cavity 27 housing the motor. The motor has a rotating shaft 26 to which a weight 28 is attached. The weight is connected to the shaft in an off center position so that when it rotates the entire device will vibrate. The top 30 of body portion 18 has a cap 32 which seals the device from the elements and provides is substantially water proof. The bottom portion 16 is removable for battery change and a slight turning of body portion 16 clockwise relative to body portion 18 causes power connecting means 22 to complete the electrical circuit from the battery to the motor causing the motor to rotate. Counterclockwise rotation disconnects the battery from the motor causing the motor to cease operation.

For the purpose of sealing the two body portions together an "O" ring, not shown, can be placed between the two body portions for sealing when assembled together.

The teeth griping interdental mouthpiece 12 constructed from a resilient material discussed above that is suitable for the purpose intended has an aperture 34 at one end for a removable friction connection to the body portion 18 by a force fit over the end of the body portion.

The interdental mouthpiece 12 has a thickness in the range of two to five millimeters and has a generally "Y" shaped plan view shaped as a dental arch with a width in the range of ten to fifteen millimeters at its distal end largest width dimension.

Figure 6:
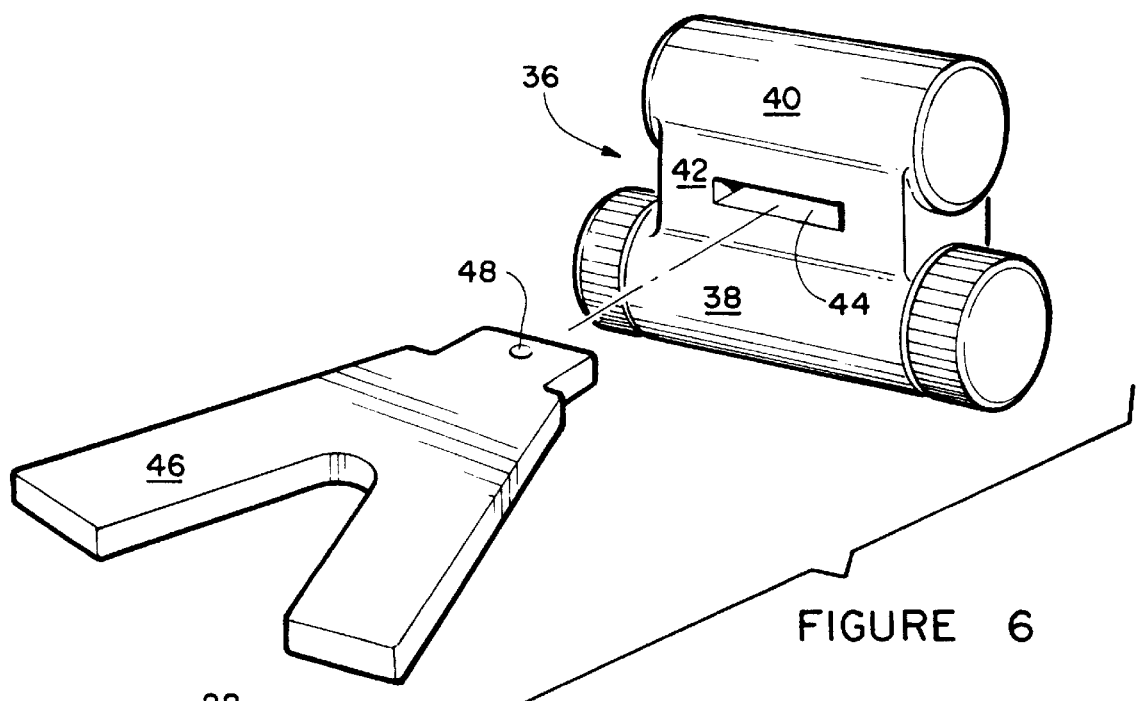
FIG. 6 depicts a second embodiment of the device of the invention with the interdental mouthpiece portion shown separated therefrom.
Figure 7:
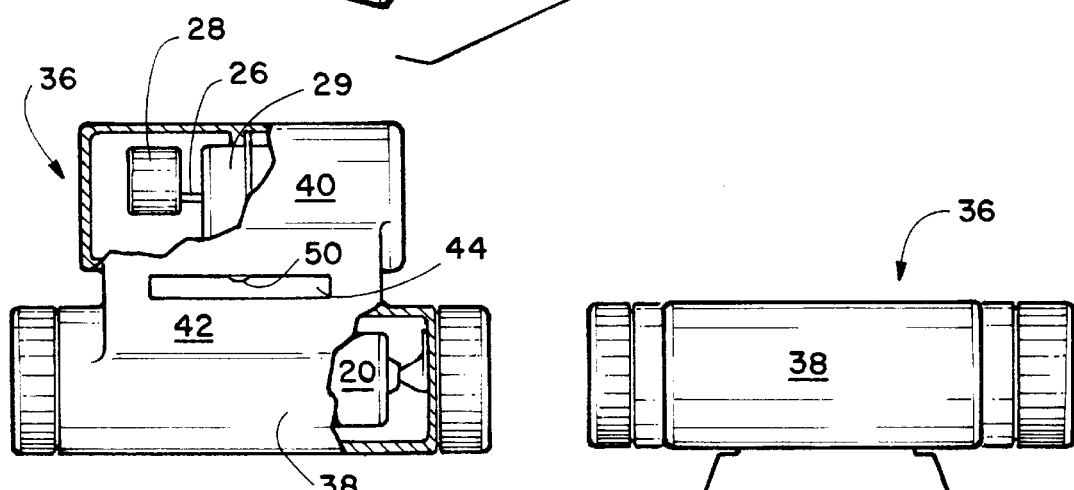
FIG. 7 is a partial cutaway side view showing of the device of Figure.
Figure 8:
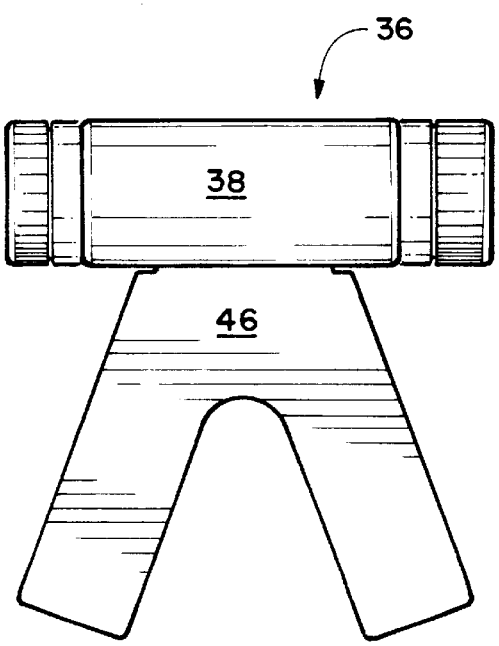
FIG. 8 is a top plan view of the device of FIG. 6 with the separated interdental mouthpiece shown inserted into the device.

FIGS. 6–8 depict a second embodiment 36 of the invention.

Referring now specifically to drawing FIG. 6, device 36 of the second embodiment includes two interconnected body portions 38 and 40 which provide the same purpose as the two body portions 16 and 18 discussed above.

Intermediate the two body portions 38, 40 at the body portions interconnector 42 having a slot 44 for receiving a interdental mouthpiece 46. The interdental mouthpiece 46 is held in place by a close fiction fit in the slot 44. A dimple 48 on either side or on both sides of the interdental mouthpiece surface registers with a protrusion 50 in the slot 44 that locks the interdental mouthpiece in slot 44. The interdental mouthpiece is removable and reinsertable by a slight force to free the connection between dimple 48 and protrusion 50.

Referring now specifically to drawing FIG. 7, the motor 24, motor shaft 26, weight 28, power supply and power connection 22 are the same as herein before described. The only significant difference between the vibrating operation of the two embodiment is that the embodiment 10 differs from embodiment 36 is that in the embodiment 10 the motor assembly is normal to the interdental mouthpiece 12 and in the embodiment 36 the motor assembly is parallel to the interdental mouthpiece 46. The resulting discomfort reduction appears to be the same in either embodiment. FIG. 8 depicts a bottom plan viewing showing of the second embodiment 36.

In operation the vibrating electric motor is activated and the patient inserts the interdental mouthpiece between their teeth and begin a clinching, releasing and sliding exercise in an attempt to engage as many teeth as possible in the transmitted vibrations.

Although it is not completely understood why there is tooth discomfort following orthodontic adjustment, it is known that the onset of discomfort is within two to four hours with a maximum discomfort level found between one and three days with a return to normal after five to seven days.

Most of the orthodontic literature concludes that pain associated with the teeth and surrounding periodontal structures is caused by the interruption of blood supply before the onset of pain. For this reason, the apparatus should be utilized as soon as possible following the orthodontic adjustment (for a period of 15 to 40 minutes). This is usually a sufficient application to eliminate the pain response in most patients. However, orthodontic adjustment of a higher force and/or adjustments to more sensitive patients can benefit from additional applications of the apparatus, such as, 10 to 15 minutes before dinner, bed, upon arising and any other time a feeling of tightness occurs.

It is believed that the high frequency vibrations transmitted to the teeth and surrounding periodontal structures via the interdental mouthpiece reestablishes a blood supply sufficient enough to eliminate the ischemic response and therefore the pain associated with post orthodontic adjustments.

The intended mouthpiece from each embodiment is easily removed which enables damaged or contaminated mouthpiece to be replaced.

It will be appreciated that while particular embodiments of the invention have been shown and described, modifications may be made. It is intended in the claims to cover the modifications which come within the spirit and scope of the invention.

What is claimed is:

1. A device for reducing the discomfort in the mouth of a human patient, said discomfort being created by the adjustment of an orthodontic appliance fitted to the patient's teeth comprising:

a housing, said housing containing a motor driven vibrating unit and a self contained power supply for operating said motor;

activating means for interconnecting said motor driven vibrating unit to said self contained power supply for operation thereof; and an elongated solid flat resilient interdental mouthpiece positioned on a plane parallel with said housing when connected thereto having substantially the shape of a dental arch and a thickness in the range of two to five millimeters removably connected to said housing, the distal end of said interdental mouthpiece designed for practical insertion into the mouth for gripping between the patient's teeth, when said vibrating unit is activated by said activating means said interdental mouthpiece vibrates said patent's teeth increasing blood flow and eliminating the ischemia response thereby reducing said discomfort.

2. The invention as defined in claim 1 wherein said interdental mouthpiece is removably received within a slot in said housing.

3. The invention as defined in claim 2 additionally comprising a lock means for removably attaching said interdental mouthpiece to said housing within said slot in said housing.

4. The invention as defined in claim 1 wherein said interdental mouthpiece has a width in the range of 10 to 15 millimeters at is longest dimension.

5. The invention as defined in claim 1 wherein said interdental mouthpiece is constructed from a soft plastic material flexible enough to adapt to the teeth of the patient and transfer sufficient vibrations from the motor driven vibrating unit to the teeth of that patient.

6. A device for reducing the discomfort in the mouth of a human patient, said discomfort being created by the adjustment of an orthodontic appliance fitted to the patient's teeth comprising:

a housing, said housing containing a motor driven vibrating unit and a self contained power supply for operating said motor;

activating means for interconnecting said motor driven vibrating unit to said self contained power supply for operation thereof; and an elongated solid flat resilient interdental mouthpiece that is removably attached to said housing on the external surface thereof adjacent to said motor driven vibrating unit by an aperture therethrough for receiving a distal end of said housing and fictionally maintaining the attachment of said interdental mouthpiece to said housing, said housing having substantially the shape of a dental arch and a thickness in the range of two to five millimeters removably connected to said housing, the distal end of said interdental mouthpiece designed for practical insertion into the mouth for gripping between the patient's teeth, when said vibrating unit is activated by said activating means said interdental mouthpiece vibrates said patent's teeth increasing blood flow and eliminating the ischemia response thereby reducing said discomfort.

7. The invention as defined in claim 6 wherein said interdental mouthpiece has a width in the range of 10 to 15 millimeters at is longest dimension.

8. The invention as defined in claim 6 wherein said interdental mouthpiece is constructed from a soft plastic material flexible enough to adapt to the teeth of the patient and transfer sufficient vibrations from the motor driven vibrating unit to the teeth of that patient.

9. The invention as defined in claim 6 wherein said interdental mouthpiece is positioned on the outer surface of said housing normal to the longest dimension of said housing.

\* \* \* \* \*